United States Patent [19]
Smith, III et al.

[11] Patent Number: 5,900,270
[45] Date of Patent: May 4, 1999

[54] TECHNIQUE FOR TESTING AND COATING A MICROPOROUS MEMBRANE

[75] Inventors: Hubert S. Smith, III, Denver; Tom L. Clark, Windsor; Laura L. McBurney, Arvada, all of Colo.

[73] Assignee: Cobe Laboratories, Inc., Lakewood, Colo.

[21] Appl. No.: 08/934,977

[22] Filed: Sep. 22, 1997

[51] Int. Cl.$^6$ .............................. B05D 3/10; B05D 5/00; B05D 7/22; G01N 27/00

[52] U.S. Cl. .............................. 427/8; 427/2.3; 427/2.31; 427/230; 427/384; 324/71.1; 324/93; 324/439

[58] Field of Search ................. 427/8, 2.3, 2.25, 427/393.5, 244, 2.31, 2.11, 2.12, 384, 230; 324/71.1, 439, 93, 72; 436/151

[56] References Cited

U.S. PATENT DOCUMENTS

| | | |
|---|---|---|
| 2,012,762 | 8/1935 | Kern . |
| 2,297,837 | 10/1942 | Loughnane ............................ 324/557 |
| 2,622,129 | 12/1952 | Killian . |
| 2,981,886 | 4/1961 | Beck . |
| 3,252,155 | 5/1966 | Surtees et al. . |
| 3,254,526 | 6/1966 | Yarbrough ................................ 73/40 |
| 3,383,863 | 5/1968 | Berry . |
| 3,414,808 | 12/1968 | Thomas . |
| 3,811,317 | 5/1974 | Leonard et al. ........................... 73/40 |
| 3,855,531 | 12/1974 | Fielibert et al. . |
| 3,937,064 | 2/1976 | Wolf, Jr. et al. ........................... 73/40 |
| 4,239,729 | 12/1980 | Hasegawa et al. ........................ 422/48 |
| 4,267,295 | 5/1981 | Gallop et al. .............................. 526/264 |
| 4,355,109 | 10/1982 | Zajic et al. ................................ 435/170 |
| 4,540,407 | 9/1985 | Dunn ........................................ 604/292 |
| 4,583,039 | 4/1986 | Kolcio et al. ............................. 324/54 |

(List continued on next page.)

FOREIGN PATENT DOCUMENTS

| | | |
|---|---|---|
| 0214614 | 3/1987 | European Pat. Off. . |
| 0323341 | 7/1989 | European Pat. Off. . |
| 1245978 | 7/1986 | U.S.S.R. . |
| 1603249 | 10/1990 | U.S.S.R. . |
| WO 92/21387 | 12/1992 | WIPO . |

OTHER PUBLICATIONS

ICI Speciality Chemicals, "Types of Surfactants From ICI Speciality Chemicals"; no date.
ICI Surfactants; "Guide to ICI Surfactants"; ICI Americas, Inc.; Feb. 1994; pp. 1–8, 21, and 24.
"Prevention of protein adsorption and platelet adhesion on surfaces by PEO/PPO/PEO triblock copolymers"; M. Amiji and K. Park; Biomaterials, 1992, vol. 13, No. 10; pp. 682–692. (no month).
"Protein resistant surfaces prepared by PEO–containing block copolymer surfactants"; Journal of Biomedical Research; vol. 23, pp. 351–368; 1989. (no month).
"Pluronic & Tetronic Block Copolymer Surfactants"; BASF Corporation, 1989, (no month).

(List continued on next page.)

Primary Examiner—Diana Dudash
Attorney, Agent, or Firm—John R. Ley; John B. Phillips

[57] ABSTRACT

The integrity of a microporous membrane within a mass transfer device such as an oxygenator is tested simultaneously with applying a biocompatible surfactant to at least the blood-contact surface of the membrane. The membrane integrity test contacts both sides of the microporous membrane with a conductive fluid to establish an electrical circuit. An electrical signal is then applied to the circuit and a measurement is taken of the test voltage across an impedance in the circuit. The value of the test voltage is used to determine the conductivity and thus the integrity of the membrane. The biocompatible surfactant is mixed with the conductive fluid used in the electrical integrity test and has an affinity for the microporous membrane material so that a durable biocompatible coating is applied to at least a portion of the microporous membrane. The biocompatible surfactant additionally reduces the drying time of the microporous membrane following the integrity test, and the surfactant may be applied to both sides of the membrane to further reduce the drying time.

35 Claims, 4 Drawing Sheets

U.S. PATENT DOCUMENTS

| | | | |
|---|---|---|---|
| 4,704,203 | 11/1987 | Reed | 210/188.5 |
| 4,705,709 | 11/1987 | Vailancourt | 427/2 |
| 4,749,585 | 6/1988 | Greco et al. | 427/2 |
| 4,810,971 | 3/1989 | Marable | 324/557 |
| 4,909,069 | 3/1990 | Albin et al. | 73/40 |
| 4,956,635 | 9/1990 | Langdon | 340/540 |
| 5,036,309 | 7/1991 | Dennison, Jr. | 340/540 |
| 5,049,275 | 9/1991 | Gillberg-LaForce et al. | 264/48 |
| 5,059,913 | 10/1991 | Nigro et al. | 324/557 |
| 5,061,738 | 10/1991 | Solomon et al. | 523/100 |
| 5,091,205 | 2/1992 | Fan | 427/412.1 |
| 5,109,215 | 4/1992 | Dennison | 340/540 |
| 5,114,425 | 5/1992 | Williams et al. | 606/34 |
| 5,135,516 | 8/1992 | Sahatjian et al. | 427/412.1 |
| 5,162,102 | 11/1992 | Nogawa et al. | 210/500.23 |
| 5,165,952 | 11/1992 | Solomon et al. | 427/2 |
| 5,196,799 | 3/1993 | Beard et al. | 324/557 |
| 5,204,632 | 4/1993 | Leach | 324/557 |
| 5,214,387 | 5/1993 | Fenner | 324/557 |
| 5,290,918 | 3/1994 | Bui-Khac | 530/381 |
| 5,295,978 | 3/1994 | Fan et al. | 604/265 |
| 5,351,008 | 9/1994 | Leach et al. | 324/557 |
| 5,395,923 | 3/1995 | Bui-Khac et al. | 530/381 |
| 5,429,802 | 7/1995 | Hagiwara et al. | 422/48 |
| 5,447,724 | 9/1995 | Helmus et al. | 427/2.12 |
| 5,451,424 | 9/1995 | Solomon et al. | 427/2.1 |
| 5,455,108 | 10/1995 | Quincy et al. | 427/538 |
| 5,477,155 | 12/1995 | Proulx et al. | 324/71.1 |
| 5,496,637 | 3/1996 | Parham et al. | 210/500.23 |
| 5,525,415 | 6/1996 | Quincy, III et al. | 428/266 |
| 5,540,984 | 7/1996 | Quincy, III et al. | 428/266 |
| 5,569,463 | 10/1996 | Helmus et al. | 424/426 |
| 5,584,875 | 12/1996 | Duhamel et al. | 427/430.1 |
| 5,643,681 | 7/1997 | Voorhees et al. | 428/483 |

OTHER PUBLICATIONS

"BASF Performance Chemicals"; BASF Corporation, 1991. (no month).

Technical Bulletin, "Plurafac RA–20 Linear Alcohol Alkoxylate"; Industrial and Performance Chemicals; BASF Corporation; 1987. (no month.

Article, "Microemboli Observed in Deaths Following Cardiopulmonary Surgery: Silicone Antifoam Agents and Polyvinyl Chloride Tubing as Sources of Emboli"; Orensetine et al.; Human Pathology; vol. 13, No. 12, Dec. 1982, pp. 1082–1090.

Article, "A comparison of Pluronic F–68, low molecular weight dextran, mannitol, and saline as priming agents in the heart–lung apparatus, Part I Pluronic F–68; First use as a plasma substitute"; Hymes et al. ; Journal of Thoracic and Cardiovascular Surgery; vol. 56, No. 1; Jul. 1968; pp. 16–22.

Chapter 10, "Polyalkylene Oxide Block Copolymers"; Nonionic Surfactants; pp. 300–371; 1967. (no month).

Article, "Adjunctive Use of a Surface–Active Agent in Extracorporeal Circulation"; Yoshimasa et al.; Supplement to Circulation, vol. XXXIII and XXXIV, Apr. 1966, pp. I–71 to I–77.

Article, "Fat globulemia in extracorporeal circulation", Wright et al.; Surgery, Apr. 1963, pp. 500–504.

TECHNIQUE FOR TESTING AND COATING A MICROPOROUS MEMBRANE

The present invention relates to a new and improved technique for leak testing and coating microporous membranes used within mass transfer devices, such as membrane oxygenators, by contacting both sides of the microporous membrane with a conductive fluid and passing an electrical current across the microporous membrane, while simultaneously mixing a biocompatible surfactant within the conductive fluid to durably coat at least one side of the microporous membrane with the surfactant. Measuring the electrical current passed through the membrane determines the integrity or ability of the microporous membrane to prevent leaks when the mass transfer device is used in a medical procedure. The surfactant reduces the time required to dry the microporous membrane at the conclusion of the test and enhances biocompatibility of the microporous membrane for contact with blood or other body fluids when the mass transfer device is used.

BACKGROUND OF THE INVENTION

Mass transfer devices used in the medical field typically utilize a microporous membrane as a substitute for the natural function of an organ or tissue of a human body. For example, a microporous membrane oxygenator provides a substitute for a patient's lung functions. While the present invention may be applied to a variety of different microporous membrane mass transfer devices, the preferred embodiment of the present invention is described below with respect to microporous membrane oxygenators.

Microporous membranes are typically formed from a hydrophobic material such as polypropylene and include micropore structures of a size significantly smaller than blood cells. Microporous membrane oxygenators thus allow gas to be exchanged across the membrane while preventing significant infiltration or wetting of the membrane pores by a patient's blood plasma over the course of a cardiopulmonary bypass procedure.

The manufacture of both flat sheet and hollow fiber microporous membrane oxygenators requires a relatively complex process which includes cutting the fragile microporous membrane material and sealing or "potting" that material within a housing to form opposing fluid-containing (i.e., blood and gas) compartments separated by the microporous membrane. Additionally, due to the critical medical applications for which microporous membrane oxygenators are used, each completed oxygenator must be tested to verify the integrity of the microporous membrane material and the seals within the housing to ensure that the gas and the blood can not leak between the two separate compartments. Such leak testing is an integral part of the manufacturing process for any microporous membrane mass transfer device such as microporous membrane oxygenators.

Previous methods for testing the integrity of microporous membranes used within oxygenators typically require charging one side of the microporous membrane (e.g., the "blood compartment" of a membrane oxygenator) with pressurized water and then visually observing the other side of the microporous membrane (e.g., the "gas compartment" of a membrane oxygenator) for water leaking across or around the membrane. If no visual evidence of water or water vapor is observed within a predetermined time interval (e.g., five minutes for a hollow fiber oxygenator or fifteen minutes for a flat sheet oxygenator), the leak-test is concluded and the oxygenator is passed on to a final sterilization process prior to shipping. However, if water is detected on the opposite side of the microporous membrane during the course of the test, the microporous membrane is considered defective and the entire oxygenator is discarded.

The above-described visual leak testing method suffers from several disadvantages. First, the leak test is relatively slow in that it requires 5–15 minutes to complete, after which the microporous membrane must be allowed to dry completely. Drying typically requires a relatively longer period of time (e.g., an additional 10–12 minutes for a hollow fiber oxygenator and an additional 90 minutes for a flat sheet oxygenator). Thus, the total time required for testing and drying a flat sheet microporous membrane utilizing the prior-art leak test is approximately 105 minutes, during which time the newly manufactured mass transfer device must remain within the manufacturing clean room. This represents a significant manufacturing cost, particularly in light of the cost of clean room facilities.

A second disadvantage is that the prior art leak-test method is labor intensive due to its reliance on trained technicians to visually detect leaks within the microporous membrane device. Additionally, due to the production-line nature of the manufacturing process, it is possible that even a trained technician will fail to notice small leaks in some membranes (i.e., a "false negative" result). On the other hand, it is also possible for technicians to incorrectly conclude that condensation which forms in the gas compartment of the oxygenator is the result of a water leak through a defective membrane (i.e., a "false positive" result). However, such condensation is not uncommon when warm air is used to blow the water out of the blood side of the oxygenator and dry the membrane (i.e., the warm air may cause water vapor to pass through the microporous membrane where it cools and condenses in the gas side of the oxygenator). Furthermore, this visual leak test provides little or no capability to detect weakened or compromised microporous membranes which nevertheless retain enough integrity to avoid passing fluid during the course of the test, but which have an elevated risk of failure during the typical prolonged period of use involved in a medical procedure such as cardiopulmonary bypass.

Improvements in the accuracy of such visual leak tests have been attempted by employing an electrical circuit to automate the testing process. For example, it is well known in the art of rubber glove testing that the a glove may be filled with water and dipped in an electrolyte bath to which a voltage has been applied. If an electrode placed within the glove detects current flowing through the circuit completed by the electrolyte bath on the exterior of the glove, a defect (such as a tear or a pinhole) is indicated and the glove is discarded. A related method used for testing the integrity of microporous membranes is described in U.S. Pat. No. 5,477,155, issued Dec. 19, 1995, for a CURRENT FLOW INTEGRITY TEST ("the '155 Patent"). In brief, the '155 Patent discloses a process for verifying the integrity of and for analyzing the pore-size distribution of porous membranes and membrane filters. The '155 Patent describes contacting both sides of the porous membrane with a liquid and applying an electrical potential across the membrane. The pressure on at least one side of the membrane is gradually increased and changes in electrical conductivity across the porous membrane are measured to determine a distribution of the different pore sizes within the porous membrane. In essence, the conductivity across the porous membrane rises as the pressure of the liquid rises and the pores of smaller size are intruded or wetted. Using this method, defects within the porous membrane (corresponding to pores of excessive size) can be detected before the pressure applied to the porous membrane exceeds a characteristic intrusion or wetting pressure which corresponds to the intrusion or wetting of the largest pores normally present within the porous membrane.

Regardless of whether a visual or electrical test is used to determine the integrity of a microporous membrane, once a membrane oxygenator has been successfully tested and dried, it is sometimes desirable to subject the oxygenator to additional manufacturing processing, such as the application of a biocompatible material to the membrane and other blood contact surfaces of the oxygenator. For example, U.S. Pat. No. 5,643,681, issued Jul. 1, 1997, for a BIOCOMPATIBLE COATED ARTICLE and assigned to the assignee hereof ("the '681 Patent"), describes a process for coating blood contact surfaces within oxygenators or similar mass transfer devices to improve the biocompatibility of the device relative to a similar uncoated device. In general, biocompatibility reduces the trauma or damage to components of the blood or other body fluids, such as blood cells, which will typically result from the contact of the blood or fluid with a non-natural surface. Specifically, the '681 Patent describes a process of coating an assembled and leak-tested oxygenator with a solvent containing a triblock copolymer known commercially as SMA-423 (see column 8, lines 29–61). The '681 Patent notes that several advantages arise from applying the biocompatible coating after oxygenator assembly (or at least after assembly of the separate components such as the oxygenation compartment and the heat exchanger) as opposed to using pre-coated membranes and heat exchangers. These advantages include reduced manufacturing costs and a reduction in the amount of wasted coating material since the coating is not applied to defective oxygenators such as those oxygenators which do not pass the leak test.

Thus, the membrane coating process described in the '681 Patent occurs only after a successful membrane leak test has been completed and further requires a separate cycle of filling the blood compartment of the membrane oxygenator with the biocompatible solvent and then allowing the membrane to dry completely. To ensure that the biocompatible coating is durably applied to the membrane so that the coating does not dissolve in contact with blood, the '681 Patent further describes an additional step of exposing the coated membrane to ionizing radiation which was found to tenaciously adhere the particular biocompatible coating to the surface of the membrane. Thus, while the '681 Patent describes a process for applying a biocompatible coating to a microporous membrane oxygenator, the process requires at least two additional post-assembly steps following the membrane leak test to both apply the coating and then ensure the adherence of the coating.

Aside from the application of biocompatible coatings, it is also known to apply surface active agents or "surfactants" to a microporous membrane oxygenator to enhance the wettability of the microporous membrane and thereby speed the priming or debubbling process required before the oxygenator can be used to treat a patient. An example of such a reference is U.S. Pat. No. 5,162,102, issued Nov. 10, 1992, for a MEDICAL INSTRUMENT AND PRODUCTION THEREOF ("the '102 Patent"). The '102 Patent describes a process of manufacturing a microporous membrane oxygenator in which a surfactant is deposited onto the membrane and other blood contact surfaces to speed air removal during a priming operation. The particular surfactant described in the '102 Patent (Pluronic F-68) is a solid surfactant which dissolves within the priming solution so that it may be distributed over all of the of the blood contact surfaces of the oxygenator as the priming solution is recirculated through the oxygenator. The '102 Patent further describes that the surfactant ensures efficient priming of the blood contact surfaces (including the microporous membrane) by increasing the wettability of those surfaces, thereby allowing the priming liquid to pass over the blood contact surfaces without leaving fine bubbles adhered to the surfaces.

The '102 Patent also describes a number of methods for depositing the solid surfactant onto the oxygenator blood contact surfaces, including blowing a surfactant powder against the blood contact surfaces and, alternatively, mixing the surfactant with the test liquid used during the membrane leak test and then drying the oxygenator after the test to remove the test liquid and leave the solid surfactant deposited on the membrane. However, when the F-68 surfactant is added to the test liquid during the leak test, the '102 Patent describes that the surfactant improves the wettability of the membrane and thereby increases the sensitivity of the leak test by allowing the test liquid on the blood side of the membrane to leak more easily through pinholes in the membrane (see column 9, lines 31–33 of the '102 Patent).

Regardless of whether the surfactant is applied as a powder or as a residue following a leak test, the '102 Patent only requires that the surfactant be deposited within the oxygenator housing so that it may ultimately mix with and dissolve within the priming solution to prevent adhesion of bubbles to the blood contact surfaces during priming (see column 7, lines 12–28 of the '102 Patent). Thus, the solid surfactant described within the '102 Patent beneficially enhances the wettability of the oxygenator blood contact surfaces to both improve the priming process and also increase the sensitivity and effectiveness of the membrane leak test (by increasing the wettability of the membrane to allow the test liquid to more easily pass through the membrane and indicate defects) when the surfactant is mixed with the test liquid. However, the surfactant of the '102 Patent does not appear to have any lasting effects following the priming process in which the surfactant is dissolved with the priming solution. Specifically, it does not appear that the disclosed surfactant (Pluronic F-68) remains adhered to the blood contact surfaces of the oxygenator following the priming process, nor is there any suggestion that the Pluronic surfactant could be applied as a coating to the blood contact surfaces to enhance the biocompatibility of those surfaces. Rather, the Pluronic surfactant is only disclosed as a wetting agent for removing air bubbles and increasing the sensitivity of the membrane leak test.

Thus, while the prior art describes processes for applying biocompatible coatings to microporous membrane oxygenators, these processes require additional steps which significantly increase the complication of the membrane oxygenator manufacturing process. Additionally, while other prior art processes provide for beneficially depositing surfactants onto blood contact surfaces of a microporous membrane oxygenator without adding additional steps to the manufacturing process (e.g., mixing the surfactant with the test liquid during the membrane leak test), these processes do not provide for the durable application of a surfactant to such blood contact surfaces, nor do they provide for enhancing the biocompatibility of those surfaces.

These and other considerations have contributed to the evolution of the present invention which is summarized below.

SUMMARY OF THE INVENTION

In light of the shortcomings of the above-described prior art membrane leak tests, a new leak-test method is needed which would increase the accuracy of the leak test by reducing or eliminating the possibility of human error while also reducing the time required for testing each individual mass transfer device. Furthermore, a new method is needed for efficiently applying biocompatible coatings to microporous mass transfer devices while not increasing the length or complexity of the manufacturing and testing process.

One of the significant aspects of the present invention pertains to a method of performing an electrical leak test of a microporous membrane mass transfer device, such as a microporous membrane oxygenator. The electrical leak test includes contacting both sides of the microporous membrane with electrically conductive fluid and then energizing an electrical circuit which includes the conductive fluid and the microporous membrane itself. The microporous membrane is considered to be defective if a significant test voltage is detected. The electrical leak test is more accurate and can be conducted far more quickly than prior visual integrity tests.

A further significant aspect of the present invention is the application of a surfactant to at least one surface of the microporous membrane during the electrical leak test by mixing the surfactant with the electrically conductive fluid used to conduct the leak test. The surfactant has the beneficial property of reducing the time required to air dry the microporous membrane following the electrical leak test.

Another significant aspect of the present invention is the choice of a biocompatible surfactant which has an affinity for microporous membranes and which remains durably adhered to the microporous membrane following the process of testing and air drying the microporous membrane. The biocompatible surfactant thus remains deposited as a coating on at least a portion of the blood contact surface of the microporous membrane. Furthermore, the biocompatible surfactant preferably demonstrates a greater biocompatibility than that of the microporous membrane material alone, and thus the surfactant provides for a reduction in blood trauma when the microporous membrane mass transfer device is subsequently utilized to treat a patient.

A still further significant aspect of the present invention is that the above beneficial effects may be achieved while using a relatively small amount of the surfactant which does not compromise the electrical membrane leak test by prematurely wetting the microporous membrane during the course of the test. Furthermore, the biocompatible surfactant which is used during the electrical leak test and which is ultimately deposited as a coating on a portion of the microporous membrane does not adversely affect the performance of the microporous membrane mass transfer device.

A more complete appreciation of the present invention and its scope may be obtained from the accompanying drawings, which are briefly summarized below, from the following detailed descriptions of presently preferred embodiments of the invention, and from the appended claims.

DETAILED DESCRIPTION

The present invention involves a method of testing the integrity of a microporous membrane mass transfer device while simultaneously coating the microporous membrane with a surfactant which adheres to the microporous membrane to enhance the biocompatibility of the microporous membrane when the membrane later comes in contact with a patient's blood. Additionally, the surfactant does not interfere with the operation or results of the electrical leak test, although the surfactant does significantly reduce the membrane drying time following the leak test. These different aspects of the present invention (i.e., the reduced drying time following the electrical leak test and the biocompatible coating which is applied to the membrane following the leak test) both rely on the application of the surfactant during the course of the leak test. However, these different aspects are discussed separately below and sample test data will be supplied to demonstrate both the enhanced speed and accuracy of the electrical leak test as well as the biocompatible nature of the surfactant coating.

Electrical Leak Test

Figure 1:
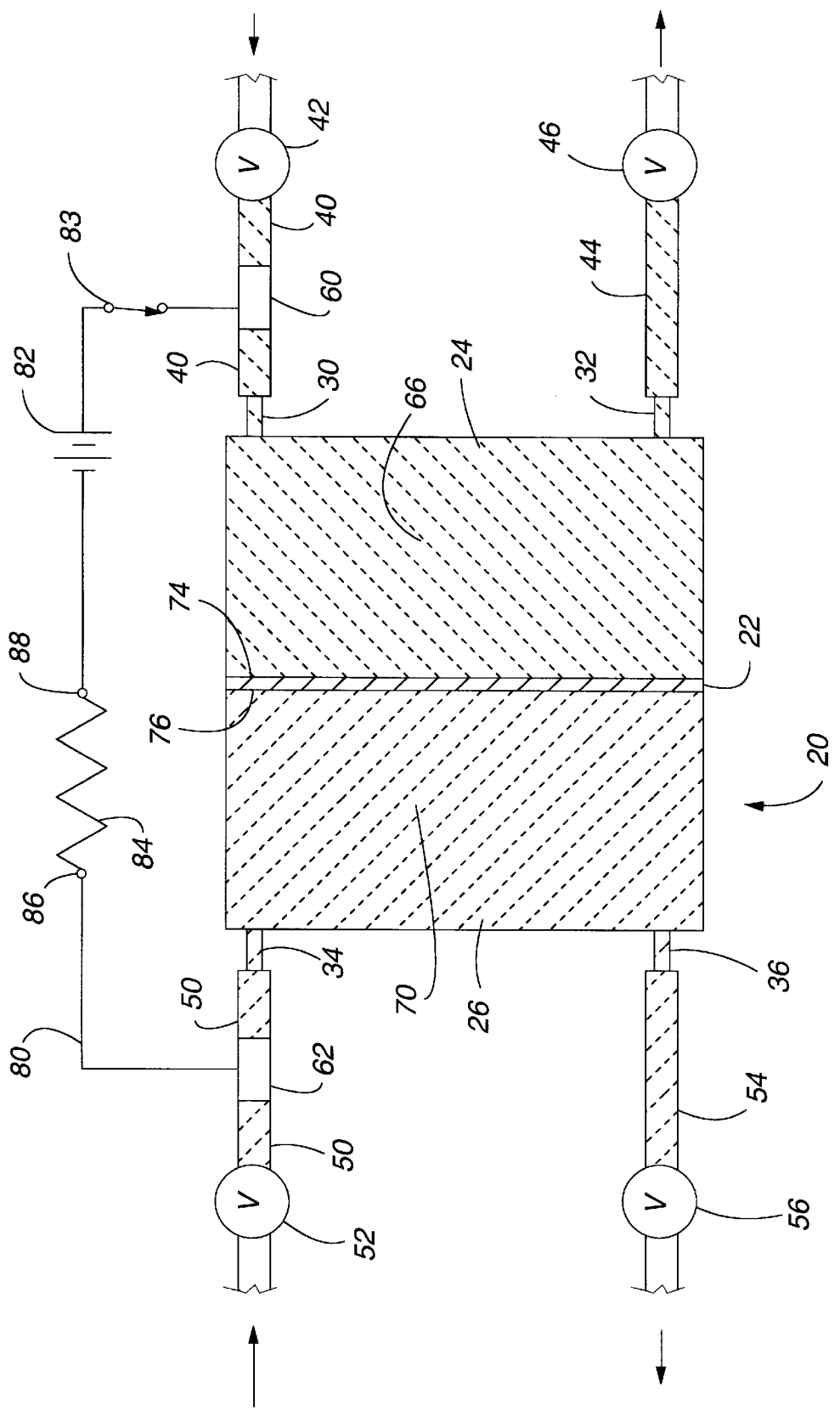
FIG. 1 is a schematic view of a microporous membrane mass transfer device connected to a test circuit by which to practice the process of the present invention to test the integrity of the microporous membrane and simultaneously coat the membrane with a biocompatible surfactant.

The method of the present invention is best shown by the test circuit illustrated in FIG. 1. The schematic view of a microporous membrane oxygenator 20 in FIG. 1 illustrates a microporous membrane 22 separating the oxygenator 20 into first and second compartments 24 and 26, respectively. The first compartment 24 corresponds to the blood side of the microporous membrane 22 while the second compartment 26 corresponds to the gas side of the microporous membrane 22. As noted above, the present invention may also be beneficially applied to other types of microporous membrane mass transfer devices and is not limited to its preferred use with microporous membrane oxygenators. Additionally, as explained in detail below, the benefits available from the present invention are applicable to microporous membrane oxygenators 20 that include either a flat sheet or a hollow fiber microporous membrane 22.

With respect to the microporous membrane oxygenator 20 in FIG. 1, the first compartment 24 includes a blood inlet port 30 and a blood outlet port 32. Similarly, the second compartment 26 includes a gas inlet port 34 and a gas outlet port 36. A first test-fluid inflow line 40 is attached at one end to the blood inlet port 30 and at an opposite end to a first inlet valve 42. Likewise, a first test-fluid outflow line 44 is attached at one end to the blood outlet port 32 and at an opposite end to a first outlet valve 46. On the opposite side of the microporous membrane 22, a second test-fluid inflow line 50 is attached at one end to the gas inlet port 34 of the oxygenator 20 and at an opposite end to a second inlet valve 52. Finally, a second test-fluid outflow line 54 is attached at one end to the gas outlet port 36 and at an opposite end to a second outlet valve 56.

First and second cylindrical metal or conductive tube electrodes 60 and 62 are preferably inserted along the length of the first and second test-fluid inflow lines 40 and 50, respectively. In this manner, the electrodes 60 and 62 combine with the inflow lines 40 and 50 to form continuous fluid flows path between the respective inlet valves 42 and 52 and the respective inlet ports 30 and 34. The first inlet valve 42 is preferably connected to a source (not shown) of a first electrically conductive fluid 66, while the second inlet valve 52 is preferably connected to a source (not shown) of a second electrically conductive fluid 70. Through operation of the first inlet valve 42 and the first outlet valve 46, the first compartment 24 and the first inflow line 40 may be filled with the first electrically conductive fluid 66 so that the first conductive fluid 66 contacts both a first surface 74 of the microporous membrane 22 as well as the first electrode 60, as illustrated in FIG. 1. Similarly the second inlet valve 52 and second outlet valve 56 may be operated to fill the second compartment 26 and the second inflow line 50 with the second electrically conductive fluid 70 so that the second conductive fluid 70 contacts both a second surface 76 of the microporous membrane 22 as well as the second electrode 62.

An electrical circuit 80 is connected between the two electrodes 60 and 62 and includes a DC voltage source 82, a switch 83, and a resistor 84. Furthermore, when the first and second compartments 24 and 26 are filled with the first and second electrically conductive fluids as described below, the circuit 80 includes the electrically conductive fluid in each of the compartments 24 and 26 in addition to the microporous membrane 22 itself. The components of the oxygenator 20, as well as the valves (42, 46, 52 and 56) and the lines (40, 44, 50 and 54) are electrical insulators, thereby causing the electrical circuit 80 to include only the voltage source 82, the switch 83, the first tube electrode 60, the first conductive fluid 66 in the first compartment 24, the pores within the microporous membrane 22, the second conductive fluid 70 in the second compartment 26, the second tube electrode 62, and the resistor 84.

The leak test of the present invention is initiated by opening the inlet valves 42 and 52 to fill the compartments 24 and 26 as described above. The valves 42 and 52 are preferably opened sequentially rather than simultaneously so that the first compartment 24 is filled slightly before the second compartment 26, thereby allowing any air bubbles trapped against the microporous membrane 22 to be pushed across the membrane into the second compartment 26. Once the second compartment 26 has been filled with the second electrically conductive fluid 70, the outlet valves 46 and 56 are preferably closed to maintain the compartments 24 and 26 and the inflow lines 40 and 50 filled with electrically conductive fluid as shown in FIG. 1. Next, the inlet valves 42 and 52 are preferably closed to electrically isolate the circuit 80 while ensuring contact between the electrically conductive fluids 66 and 70 and their respective electrodes 60 and 62, as shown in FIG. 1. Furthermore, the fluids 66 and 70 are preferably not pressurized above ambient pressure and no pressure differential exists between the two fluid 66 and 70 (i.e., no pressure differential is applied across the microporous membrane 22).

Once the two compartments 24 and 26 have been filled with their respective electrically conductive fluids 66 and 70, the electrical circuit 80 will remain essentially open (non-conductive) provided that the microporous membrane 22 is not defective (i.e., it does not include any holes or tears), and further provided that the electrically conductive fluids 66 and 70 do not remain in contact with the membrane 22 for a sufficiently long period such that the non-defective microporous membrane 22 becomes wetted, thereby allowing the first and second electrically conductive fluids 66 and 70 to contact one another. Therefore, the electrical leak test of the present invention is preferably performed over a relatively short period of time on the order of one minute, during which time the pores of the membrane 22 do not wet.

In order to determine if a microporous membrane 22 is defective, the switch 83 is closed and the voltage source 82 applies a voltage to the circuit 80 once the compartments 24 and 26 have been filled with the electrically conductive fluids 66 and 70. A test voltage is then measured across the resistor 84 between the points 86 and 88 shown in FIG. 1. The size of the test voltage across the resistor 84 determines the amount of current flowing through the microporous membrane 22 and thus the conductivity of the membrane 22. While an integral or non-defective microporous membrane 22 would ideally prevent almost any current from flowing through the circuit 80 and would therefore register as creating a negligible test voltage across the resistor 84, it has been empirically determined that some non-defective membranes will display a small test voltage during the electrical leak test. However, the typical magnitude of the test voltage for these non-defective microporous membranes is much smaller than the typical magnitude of the test voltage experienced with defective or leaky membranes. Thus, a predetermined threshold test voltage value is empirically determined so that any measured test voltage which exceeds that threshold value signifies an excessive amount of current passing through the microporous membrane 22 and thus a defective membrane. The variable nature of the test voltage achieves a high degree of precision and resolution in the evaluation and determination of the integrity of the membrane.

Figure 2:
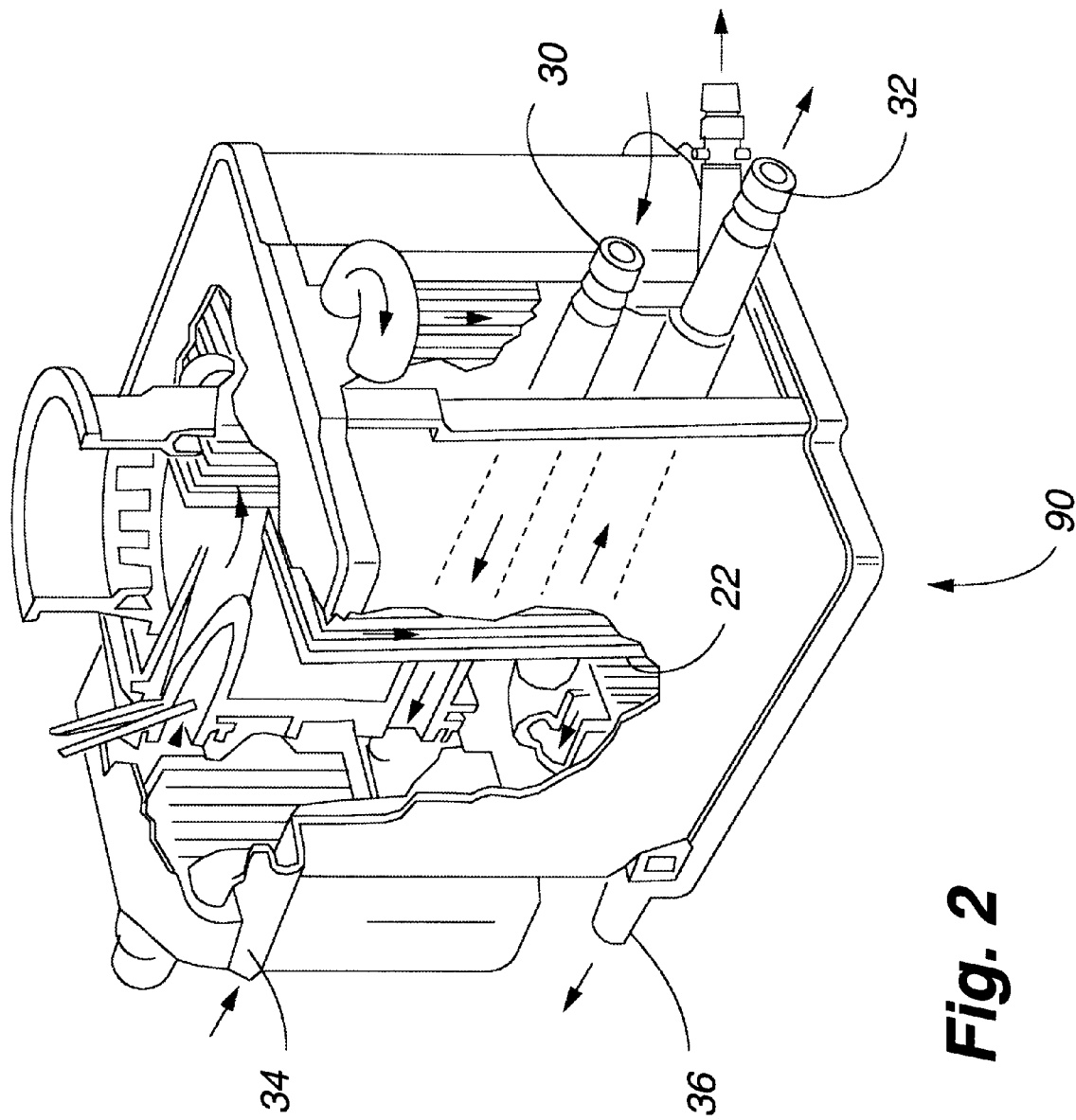
FIG. 2 is a perspective view of a flat sheet microporous membrane oxygenator which may be connected to the test circuit illustrated in FIG. 1, with portions broken away to show details of the flat sheet microporous membrane.

Of course, the value of the predetermined threshold for the test voltage depends on the value of the voltage source 82, the size of the resistor 84, the composition and geometry (i.e., flat sheet of hollow fiber) of the microporous membrane 22, and the specific conductivity of the first and second electrically conductive fluids 66 and 70. For example, when the preferred embodiment of the present invention is used with a flat sheet microporous membrane oxygenator 90 shown in FIG. 2 (a COBE® CML Duo™ oxygenator manufactured by COBE Cardiovascular, Inc., Arvada, Colo.), wherein the membrane 22 is formed from a microporous polypropylene material, it has been empirically determined that using first and second electrically conductive fluids 66 and 70 with different conductivity levels (i.e., forming a conductivity gradient across the membrane 22) allows for greater distinction between test voltage values for defective membranes and test voltage values for non-defective membranes. In this case, the first electrically conductive fluid 66 preferably constitutes a saline solution having 0.25% NaCl by weight and a conductivity in the range of 8.5–8.8 millimhos, while the second electrically conductive fluid 70 preferably constitutes water with no NaCl and a conductivity in the range of 10–40 micromhos. Additionally, the DC voltage source 82 is preferably rated at 44 volts, while the value of the resistor 84 is approximately 5 M ohms. These preferred values were empirically determined by comparing the measured test voltage across the resistor 84 with the results of prior art leak tests on the same microporous membrane oxygenators. These empirical tests result in average test voltage values for defective membranes which are approximately an order of magnitude greater than the average values for non-defective membranes. Specifically, when the above preferred values are used, the predetermined threshold test voltage across the resistor 84 is approximately 9.5 volts. Thus, if the measured test voltage across the resistor 84 is 9.5 volts or higher for the COBE® Duo™ flat sheet microporous membrane oxygenator 90 as shown in FIG. 2, then the oxygenator 90 fails the electrical leak test and is considered to be defective. However, if the measured test voltage is less than 9.5 volts, the flat sheet Duo™ oxygenator 90 passes the leak test and the microporous membrane 22 is considered to be non-defective.

Table 1 included immediately below illustrates a number of sample leak tests using the test circuit shown in FIG. 1 with the COBE® Duo™ flat sheet microporous membrane oxygenator 90 shown in FIG. 2. The flat sheet Duo™ oxygenator 90 includes dual oxygenation compartments (a primary and a secondary compartment, each containing a separate flat sheet microporous membrane). The two separate compartments may be connected in series when the oxygenator 90 is used with a large patient or, alternatively, the primary compartment may be used without the secondary compartment when treating smaller patients, thereby matching the required gas transfer capacity to the patient size reducing hemodilution. Thus, the electrical leak test of the present invention preferably tests the integrity of each membrane compartment separately and, if either compartment registers a test voltage across the resistor 84 of 9.5 volts or greater, the entire oxygenator 90 fails the leak test. Table 1 includes a separate columns indicating the measured test voltages for each of the primary and secondary oxygenation compartments, and also includes a final column which denotes the results of a previous visual leak test on each of the sample oxygenator units. Note the discrepancies in several of the test results (denoted by an asterisk (*) in the final column) which tend to demonstrate the improved accuracy of the leak test of the present invention. In essence, the first three asterisks denote occasions where the prior art visual leak test returned a false positive result (i.e., failing a non-defective membrane), where the final asterisk denote a false negative result where the prior art visual test passed a defective membrane. Where discrepancies between the two tests occurred, a more thorough visual inspection was undertaken and in each case the electrical leak test was confirmed. Thus, Table 1 clearly demonstrates the greater accuracy achieved by the electrical leak test of the present invention in relation to the prior art visual leak test.

TABLE 1

Comparison of Electrical and Visual Leak Tests

| Unit ID | Primary Compartment (volts) | Secondary Compartment (volts) | Electrical Leak Test (pass/fail) | Visual Leak Test (pass/fail) |
| --- | --- | --- | --- | --- |
| BCOBHM | 28.5 | 9.2 | F | F |
| BCOBHO | 13.0 | 5.0 | F | F |
| BCOBDJ | 0.0 | 10.7 | F | F |
| BCOBE3 | 0.8 | 19.2 | F | F |
| BCOBNK | 17.5 | 7.0 | F | F |
| AC158C | 0.0 | 0.0 | P | *F |
| AC156C | 28.8 | 24.0 | F | F |
| BCOAOM | 30.8 | 2.4 | F | F |
| AC14JC | 0.0 | 29.5 | F | F |
| AC158B | 18.2 | 0.0 | F | F |
| BCOBEQ | 0.0 | 0.0 | P | *F |
| BCOBVJ | 22.7 | 4.1 | F | F |
| BCOBY8 | 0.0 | 19.4 | F | F |
| BCOCO4 | 31.5 | 0.0 | F | F |
| BCOAO5 | 31.7 | 2.4 | F | F |
| BCOAYS | 0.0 | 0.0 | P | *F |
| BCOBT1 | 0.5 | 3.3 | P | P |
| BCOB4W | 0.0 | 0.0 | P | P |
| BCOBV3 | 0.0 | 2.1 | P | P |
| BCOBD6 | 0.6 | 2.0 | P | P |

TABLE 1-continued

Comparison of Electrical and Visual Leak Tests

| Unit ID | Primary Compartment (volts) | Secondary Compartment (volts) | Electrical Leak Test (pass/fail) | Visual Leak Test (pass/fail) |
| --- | --- | --- | --- | --- |
| BCOB4T | 9.5 | 2.3 | F | *P |
| BCOBRV | 0.0 | 2.6 | P | P |
| BCOBC5 | 0.0 | 0.0 | P | P |
| AC154M | 0.0 | 1.7 | P | P |
| BCOB61 | 0.0 | 5.7 | P | P |

Figure 3:
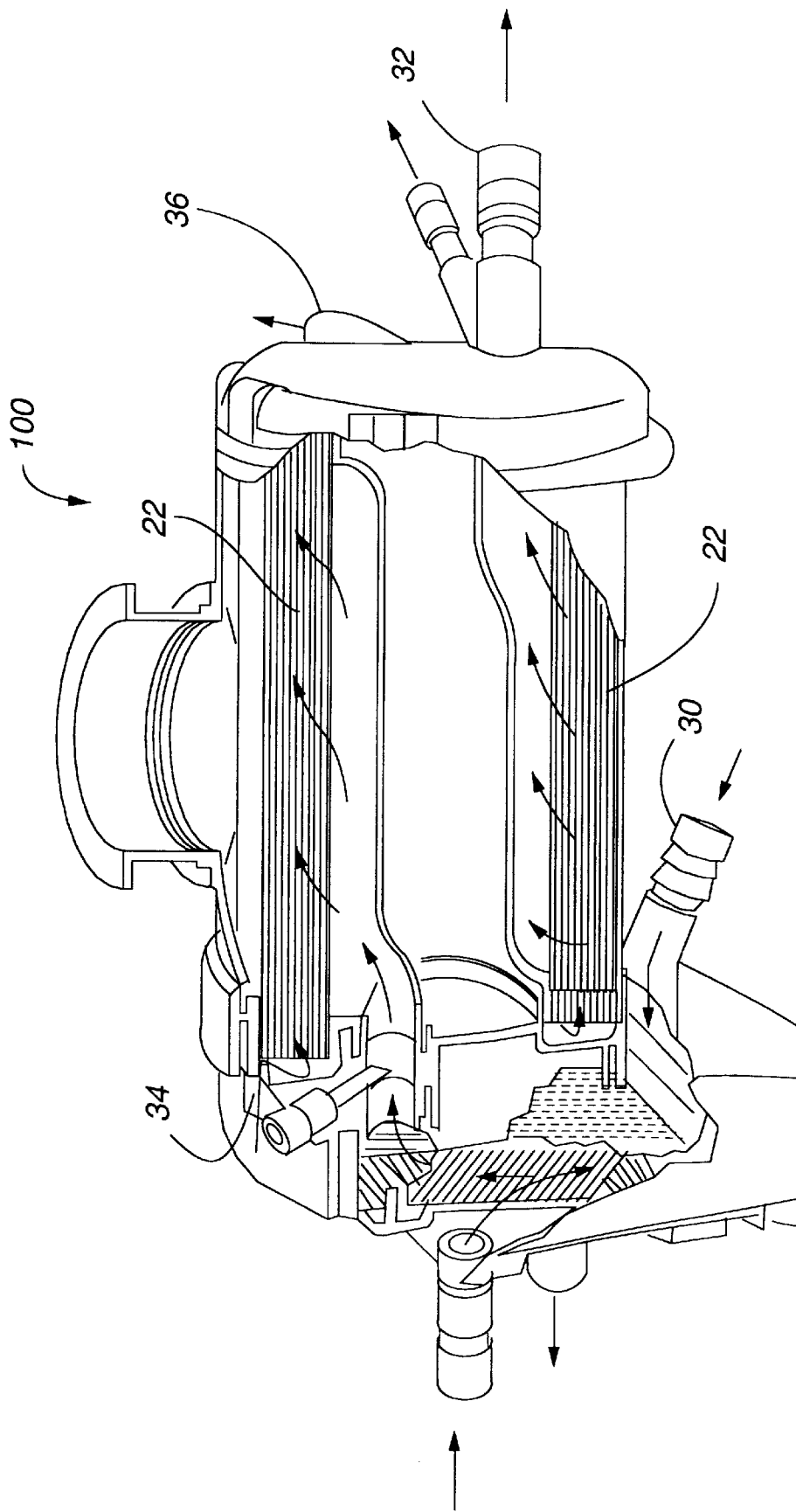
FIG. 3 is a perspective view of a hollow fiber microporous membrane oxygenator which may be connected to the test circuit illustrated in FIG. 1, with portions broken away to show details of the hollow fiber microporous membrane bundle.

While the above table describes the electrical leak test of the present invention with respect to the flat sheet microporous membrane oxygenator 90 shown in FIG. 2, the present invention also encompasses the testing of hollow fiber microporous membrane oxygenators such as the oxygenator 100 shown in FIG. 3. While substantially the same circuit 80 (FIG. 1) is used to conduct the electrical leak test on the hollow fiber oxygenator 100, it has been empirically determined that the preferred embodiments of the first and second electrically conductive fluids 66 and 70 both preferably comprise a saline solution having a substantially identical conductivity level so that no conductivity gradient is formed across the hollow fiber microporous membrane. Thus, when the hollow fiber microporous membrane oxygenator 100 (FIG. 3) is substituted for the flat sheet oxygenator 90 (FIG. 2) within the circuit 80 shown in FIG. 1, an identical saline solution having 0.25% NaCl by weight and a conductivity in the range of 8.5–8.8 millimhos is preferably used for both the first and second electrically conductive fluids 66 and 70.

An additional benefit of the electrical leak test of the present invention is the speed with which it can be performed. For example, the entire process of filling the compartments 24 and 26 with the first and second electrically conductive fluids 66 and 70, respectively, and measuring the test voltage across the resistor 84 requires less than two minutes and is preferably performed in less than 90 seconds. When compared with the prior art visual leak test which required approximately fifteen minutes for a flat sheet oxygenator, it can be readily appreciated that the present invention represents a large time savings over the prior art leak test. However, the present invention further provides for additional time savings with respect to the prior art visual leak tests (as well as other membrane tests such as the test described in the '155 Patent noted above) by substantially reducing the time required to dry the microporous membrane 22 following the leak test.

As noted above, surfactants are known to increase the wettability of certain substances and have been applied to blood contact surfaces to aid in priming and debubbling those surfaces (see, for example, the '102 Patent noted above). However, the present invention preferably applies a liquid or paste (i.e., a high viscosity liquid) surfactant to at least one surface of the microporous membrane 22 to speed the drying time of the membrane 22 following the electrical leak test described above. Specifically, the surfactant is applied to at least the blood side or the first surface 74 of the microporous membrane 22 due to the biocompatibility enhancing effect of the surfactant with the blood which flows through that compartment during subsequent patient treatment, as described in greater detail below. However, when leak testing oxygenators which require a relatively long drying time, it has been found that the application of the surfactant to both sides 74 and 76 of the microporous membrane 22 significantly reduces the required drying time.

The different geometries of flat sheet and hollow fiber microporous membranes require a longer drying time for a flat sheet oxygenator 90 (FIG. 2) than for a hollow fiber oxygenator 100 (FIG. 3). Indeed, the drying time for an untreated flat sheet oxygenator is approximately 90 minutes as opposed to approximately 10–12 minutes for an untreated hollow fiber oxygenator. Therefore, when leak testing a flat sheet microporous membrane oxygenator 90 as described above, the present invention preferably mixes a liquid surfactant with both the first and second electrically conductive fluids 66 and 70. However, when testing a hollow fiber microporous membrane oxygenator 100, the present invention preferably mixes the liquid surfactant with only the first electrically conductive fluid 66 because no substantial additional reduction in drying time is likely to be achieved from applying the liquid surfactant to both the surfaces 74 and 76 of the hollow fiber membrane. Thus, the addition of the liquid surfactant to only the first conductive solution 66 (i.e., in the blood compartment of the hollow fiber oxygenator 100) both contributes to a reduction of the drying time of the hollow fiber membrane (albeit to a lesser extent than the reduction experienced by the flat sheet oxygenator 90) and also acts to coat at least a portion of the blood contact surface 74 of the microporous membrane 22 for reasons described in greater detail below.

The liquid surfactant used preferably includes a number of beneficial properties such as an affinity to durably bond to a polypropylene microporous membrane as well as an ability to impart a biocompatibility enhancing effect to the membrane to reduce the level of certain blood traumas which typically occur when a patient's blood contacts the microporous membrane. The preferred surfactant should also not adversely affect any of the operating parameters of the microporous membrane oxygenator 20 (e.g., the surfactant coating should not hinder or reduce the ability of the microporous membrane 22 to transfer gas across the membrane). Although a number of different surfactants were investigated, including surfactants which have been predominantly used within extracorporeal mass transfer devices (e.g., the Pluronic F-68 surfactant described above with regard to the '102 Patent), it was surprisingly discovered that the liquid surfactant Tween 80 (the common name or chemical composition of which is Polysorbate 80, NF (polyoxyethylene 20 sorbitan monooleate), ICI Specialty Chemicals) provided the best combination of the desired properties noted above. Furthermore, through empirical evaluation, it has been determined that Tween 80 may be added to the electrically conductive fluids 66 and 70 in a range from about 0.010–0.100% by weight of those fluids, with a value of 0.025% by weight being preferred. While larger amounts of Tween 80 may be added, it is not believed that such additional use of the Tween 80 surfactant will further significantly reduce the drying time of the microporous membrane or further increase the biocompatibility enhancing effect described below.

An additional beneficial property of the Tween 80 surfactant is that it does not alter or adversely effect the electrical leak test. Specifically, the Tween 80 does not act to instantaneously wet the microporous membrane 22 during the course of the electrical leak test and thus the presence of the Tween-80 does not impact the results of the leak test. (Compare this result to those described in the '102 Patent which noted that Pluronic F-68 surfactant tended to wet the membrane during the course of the leak test thereby increasing the sensitivity of pinhole detections within the membrane.) Of course, this non-interaction effect is aided by the relatively small amount of the Tween 80 which is added to the test liquids 66 and 70 (or to just the test liquid 66 with respect to the hollow fiber oxygenator 100), and also by the relatively short duration of the electrical leak test.

Upon the conclusion of the electrical leak test by opening the switch 83 (FIG. 1), the first and second inlet valves 42 and 52 are closed and the first and second outlet valves 46 and 56 are opened to drain the corresponding electrically conductive fluids 66 and 70 from the respective compartments 24 and 26. As noted above, the Tween-80 surfactant is a liquid at ambient temperatures and pressures and includes as one of its beneficial properties an affinity for bonding to the polypropylene microporous membrane 22. Thus, even after the test liquids 66 and 70 have been drained from their corresponding compartments 24 and 26, a coating of the liquid Tween-80 will remain deposited on both sides of the microporous membrane 22 (or just the first side 66 in the case of a hollow fiber membrane 100). Once deposited in this manner, the Tween 80 surfactant coats the surface(s) of the microporous membrane 22, and thereby speeds the evaporation of the test liquid as drying air is applied to the membrane. Additionally, the Tween 80 surfactant tends to decrease the surface tension between the test liquid and the surface(s) of the microporous membrane 22 so that the surface area of the test liquid is effectively increased which further aids in draining fluid from the compartments and enhancing evaporation of the remaining fluid, thereby speeding the drying process.

Taking for example the flat sheet microporous membrane 90 in FIG. 2, it has been determined that the addition of the Tween-80 surfactant (in the above-prescribed amounts) to the test liquids 66 and 70 reduces the drying time of the flat sheet microporous membrane 22 from approximately ninety minutes to approximately fifteen minutes. A less dramatic time savings may be seen with respect to the hollow fiber membrane oxygenator 100. As noted above, an untreated hollow fiber oxygenator typically requires approximately 10–12 minutes to dry following a membrane leak test. If the Tween 80 surfactant is applied to at least the blood side of the microporous membrane 20, that 10–12 minute drying period may be reduced by at least one minute.

Thus, the electrical leak test of the present invention demonstrates an important benefit over the membrane test described in the '155 Patent due to the addition of the Tween 80 surfactant to the electrically conductive fluids 66 and 70. Specifically, the surfactant reduces membrane drying times following the disclosed membrane test. Additionally, the present invention represents an even more significant benefit with respect to the prior art visual leak test given that the duration of the electrical leak test is much shorter than that of the prior visual test. Taking for example the flat sheet membrane oxygenator 90, the prior art visual test requires a total of approximately 105 minutes (15 minutes for the visual leak test and 90 minutes to dry the membrane), while the present invention requires less than 20 minutes to both test and dry the microporous membrane 22. This represents a significant savings in time and overhead from a manufacturing standpoint by allowing a larger number of the membrane oxygenators to be leak tested and then removed from the manufacturing clean room in a given time.

Biocompatible Coating

As discussed above, important benefits of the present invention include the ability of the Tween 80 surfactant to be durably applied to the polypropylene microporous membrane 20 conjunctively with the electrical leak test, combined with the biocompatibility enhancing effect which has been displayed by such coated membranes. While a number of parameters may be studied to determine the relative biocompatibility of different materials or coatings, for the purposes of this description the specific parameters of platelet depletion and pressure excursion will be studied to determine the effectiveness of Tween 80 at enhancing the biocompatibility of a microporous membrane 20.

The biocompatibility of a blood-contacting material such as a microporous membrane 20 can be determined by the number of platelets which are activated or adhered to the blood contact surface. Such platelet activation or adhesion is not only detrimental to a patient (for example, excessive platelet activation can promote post-operative bleeding), but platelets which adhere to a microporous membrane can also reduce the effectiveness of the membrane by blocking the micropores, thereby hindering gas transfer across the membrane.

Figure 4:
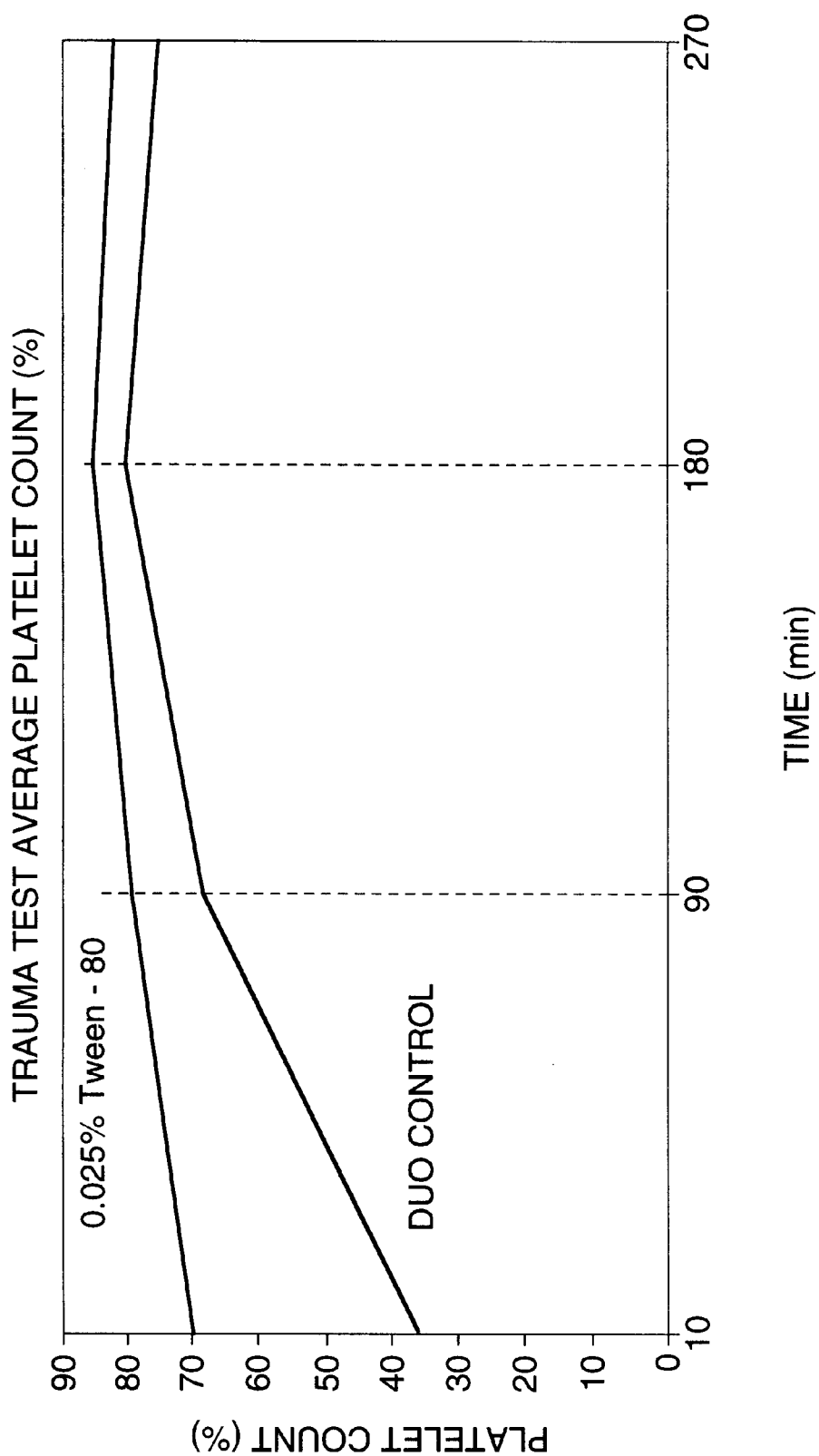
FIG. 4 is a graph illustrating a plot of average platelet counts versus time for both a control oxygenator and an oxygenator having a microporous membrane coated with the biocompatible surfactant applied during the process of the present invention.

In determining the effectiveness of the Tween 80 coating in reducing the amount of platelet activation during the course of a patient's treatment with a microporous membrane oxygenator 20, a number of trauma tests were conducted on the flat sheet Duo™ oxygenators described above. The trauma tests comprised flowing blood through two sets of Duo™ oxygenators and taking periodic platelet depletion counts. The two sets of oxygenators included a first group of control Duo™ oxygenators where the microporous membranes were not coated with any material, and a second group of Duo™ oxygenators where the microporous membrane 20 was coated with Tween 80 in the manner described above (i.e., contacting the membrane with a 0.025% by weight solution of Tween 80). The platelet depletion counts shown in Table 2 below provide an indication of the percentage of the blood platelets which remain at each of four separate time intervals (10, 90, 180 and 270 minutes). FIG. 4 illustrates a plot of the average platelet counts shown in Table 2.

TABLE 2

Trauma Test Platelet Count
(6 L/min blood flow rate through both the
primary and secondary Duo ™ membrane bundles)

| Unit ID | SUR-FACTANT COATING | 10 min. COUNT (%) | 90 min. COUNT (%) | 180 min. COUNT (%) | 270 min. COUNT (%) |
| --- | --- | --- | --- | --- | --- |
| BC05TP | CONTROL | 29 | 62 | 81 | 62 |
| BC05U9 | CONTROL | 39 | 62 | 66 | 70 |
| BC05X0 | CONTROL | 22 | 57 | 81 | 84 |
| BC0BEQ | CONTROL | 41 | 85 | 87 | 85 |
| AC0K9S | TWEEN 80 | 79 | 71 | 93 | 79 |
| AC0KD0 | TWEEN 80 | 52 | 67 | 68 | 83 |
| BC0BDY | TWEEN 80 | 89 | 81 | 74 | 70 |
| BC0BDX | TWEEN 80 | 85 | 86 | 85 | 82 |
| BC0BAF | TWEEN 80 | 88 | 72 | 84 | 74 |
| BC0B9N | TWEEN 80 | 84 | 84 | 80 | 89 |

Thus, as shown by the values in Table 2 and the average plots of those values in FIG. 4, the Duo™ oxygenators with the Tween 80 coating experienced significantly higher platelet counts (or significantly lower platelet depletion averages) than the uncoated control Duo™ oxygenators. Therefore, Table 2 and FIG. 4 demonstrate the enhanced biocompatibility effect of the Tween 80 coating which is applied during the method of the present invention.

The second indicator of biocompatibility which is examined with respect to the method of the present invention is oxygenator inlet pressure excursions resulting from platelet activation. In essence, as platelets adhere to the microporous membrane and clog the micropores of the membrane, the pressure required to maintain a constant blood flow rate through the oxygenator increases.

Pressure excursion is most easily shown by comparing pairs of control and coated membrane oxygenators at identical flow rates and using identical blood samples as shown below in Table 3. Table 3 records four different comparisons between a control (uncoated) Duo™ oxygenator and a Duo™ oxygenator where the microporous membrane is coated with Tween 80 as described above (i.e., contacted with a 0.025% by weight solution of Tween 80). As identical blood samples are circulated through each of the control and the coated units, inlet pressures are monitored and the different values included in Table 3 are calculated. For example, the first measurement represents the maximum inlet pressure recorded during the test. Since the initial inlet pressure for both the control and the coated membrane oxygenators is approximately 400–450 mmHg, it can readily be seen that a higher maximum inlet pressure represents a larger number of platelets adhered to the microporous membrane. Similarly, a higher rate of pressure increase (the next measurement in Table 3) indicates that the platelets are adhering more quickly to the uncoated microporous membrane 20. The differences between the maximum inlet pressure of the control and the coated oxygenator are divided by the maximum inlet pressure of the control oxygenator to derive the "peak excursion reduction" percentage in the next column of Table 3, while a similar calculation is performed on the pressure increase rates in the second column to derive the "pressure rate decrease" percentage in the last column.

TABLE 3

Pressure Excursion Testing
(3 L/min blood flow rate through
primary Duo ™ membrane bundle only)

| Unit ID | SUR-FACTANT COATING | Maximum Inlet Pressure (mmHg) | Rate of Pressure Increase (mmHg/min) | Peak Excursion Reduction (%) | Pressure Rate Decrease (%) |
| --- | --- | --- | --- | --- | --- |
| BC1FNF | CONTROL | 889 | 66 | 12.6 | 69.7 |
| BC1FNE | TWEEN 80 | 775 | 20 | | |
| BC1BFR | CONTROL | 803 | 48 | 13.3 | 70.8 |
| BC1BFP | TWEEN 80 | 698 | 14 | | |
| BC0S9E | CONTROL | 1069 | 95 | 26.1 | 67.4 |
| BC0PTP | TWEEN 80 | 790 | 31 | | |
| BC0T2M | CONTROL | 1084 | 106 | 19.0 | 76.4 |
| BC0U02 | TWEEN 80 | 876 | 25 | | |

Thus, as shown by the values in Table 3, the control oxygenator routinely experienced higher maximum inlet pressures and higher pressure increase rates indicating that the control or uncoated oxygenator membrane was subjected to higher levels of platelet adhesion. The last two columns of the table provide relative percentages between the control and the coated oxygenators, and these percentages clearly demonstrate that substantial biocompatibility improvements can be seen when the oxygenator membrane is coated with Tween 80. For example, the four samples included within Table 3 show that, on average, pressure excursions can be reduced by approximately 18% and pressure rate decreases of approximately 71% can be achieved when the microporous membrane is coated with Tween 80 as provided by the present invention.

While other surfactants in addition to Tween 80 are known to provide some biocompatibility enhancing effects, no other surfactant is presently known which matches the biocompatibility enhancing performance of Tween 80 as measured by the two tests described above (i.e., platelet depletion and pressure excursion). For example, the solid Pluronic F-68 surfactant provides poor results on the platelet depletion trauma test. Similarly, while one particular liquid Pluronic surfactant known as P-105 provides platelet depletion test results which are similar to the Tween 80 results, the P-105 surfactant does not match the performance of the Tween 80 in the pressure excursion tests.

Thus, the method of the present invention provides significant improvements by allowing a microporous membrane to be beneficially and durably coated with the Tween 80 surfactant as the microporous membrane undergoes an electrical leak test. The electrical leak test requires substantially less time and provides more accurate results than prior art visual leak tests. Additionally, by applying the Tween 80 surfactant during the course of the electrical leak test, the Tween 80 is available to speed the drying process of the microporous membrane following the leak test.

Furthermore, the Tween 80 coating is durably applied to the microporous membrane during the leak test to enhance the biocompatibility of the coated membrane during subsequent use of the microporous membrane oxygenator. While other microporous membrane oxygenators have attempted to apply a surfactant to their corresponding blood contact surfaces, these surfactants have not been applied to the microporous membrane in the manner of the present invention nor do these prior art surfactants include all of the above-described beneficial features of the Tween 80 surfactant. For example, the Pluronic F-68 surfactant described within the '102 Patent noted above does not bond durably to the microporous membrane since it is a solid surfactant which reportedly dissolves within the priming fluid used to debubble the membrane oxygenator prior to use. Furthermore, testing of the Pluronic F-68 surfactant indicates that it does not significantly reduce the drying time of a microporous membrane nor does it enhance the biocompatibility of a microporous membrane. Also, as discussed above, alternative "biocompatible" surfactants (e.g., the Pluronic P-105) have not proved to be as effective during trauma tests as the Tween 80 surfactant. Further still, applying such surfactants during membrane integrity tests, and using such surfactants to enhance drying the membrane following the integrity test represent substantial improvements in mass transfer device manufacturing and testing processes.

A presently preferred embodiment of the present invention and many of its improvements have been described with a degree of particularity. This description is a preferred example of implementing the invention, and is not necessarily intended to limit the scope of the invention. The scope of the invention is defined by the following claims.

The invention claimed is:

1. A method of testing the integrity of a microporous membrane within a mass transfer device while applying a surfactant coating to the microporous membrane, said microporous membrane fixed within the mass transfer device to define a first compartment in fluid communication with a first surface of the microporous membrane and a second compartment in fluid communication with a second surface of the microporous membrane, the microporous membrane including pores extending between the first and second surfaces, said method comprising the steps of:

mixing a first electrically conductive fluid with a predetermined amount of a surfactant to form a first mixture, said surfactant having an affinity for attaching to the microporous membrane;

filling the first compartment with the first mixture;

filling the second compartment with a second electrically conductive fluid;

forming an electrical circuit which includes an impedance, the microporous membrane, the first mixture and the second electrically conductive fluid;

applying a predetermined signal to the electrical circuit;

measuring a test voltage across the impedance;

selecting the predetermined amount of surfactant in the first mixture to prevent the first mixture from substantially wetting the pores of a non-defective microporous membrane before measuring the test voltage across the impedance;

comparing the measured test voltage to a predetermined threshold value;

determining the microporous membrane to be defective if the measured test voltage exceeds the predetermined threshold value and determining the microporous membrane to be non-defective if the measured test voltage does not exceed the predetermined threshold value;

draining the first mixture and the second electrically conductive fluid from the respective first and second compartments while maintaining surfactant from the first mixture deposited as a coating on the first surface of the microporous membrane; and air drying the microporous membrane for a predetermined drying time sufficient to eliminate residual first and second fluids from the microporous membrane after draining, wherein said surfactant reduces the surface tension between the microporous membrane and residual first fluid to establish the predetermined drying time for air drying the microporous membrane as less than the air drying time of the microporous membrane in the absence of the surfactant.

2. A method as defined in claim 1, wherein the surfactant remains durably deposited to at least a portion of the first surface of the microporous membrane following the step of air drying the microporous membrane, said surfactant providing a bio-compatible coating for blood contacting the first surface of the microporous membrane.

3. A method as defined in claim 2 wherein the mass transfer device is a blood oxygenator.

4. A method as defined in claim 3 wherein the microporous membrane is a flat sheet membrane.

5. A method as defined in claim 3 wherein:

the microporous membrane is a hollow fiber bundle;

the first surface of the microporous membrane is an exterior surface of the hollow fibers; and the second surface of the microporous membrane is an interior surface of the hollow fibers.

6. A method as defined in claim 5 wherein the surfactant is polysorbate 80, NF (polyoxyethylene 20 sorbitan monooleate).

7. A method as defined in claim 6 wherein the predetermined drying time is less than 10 minutes.

8. A method as defined in claim 6 wherein the first and second electrically conductive fluids have substantially the same conductivity.

9. A method as defined in claim 8 wherein the first and second electrically conductive fluids are identical.

10. A method as defined in claim 6 wherein the first and second electrically conductive fluids are pressurized to substantially the same pressure.

11. A method as defined in claim 6 wherein the first and second electrically conductive fluids are substantially at ambient pressure.

12. A method as defined in claim 6 wherein the predetermined amount of the surfactant in the first mixture is within a range of approximately 0.010% to 0.100% by weight of the first electrically conductive fluid.

13. A method as defined in claim 12 wherein the predetermined amount of the surfactant in the first mixture is approximately 0.025% by weight of the first electrically conductive fluid.

14. A method of testing the integrity of a microporous membrane within a mass transfer device while applying a surfactant coating to the microporous membrane, said microporous membrane fixed within the mass transfer device to define a first compartment in fluid communication with a first surface of the microporous membrane and a second compartment in fluid communication with a second surface of the microporous membrane, the microporous membrane including pores extending between the first and second surfaces, said method comprising the steps of:

mixing predetermined amounts of a surfactant with first and second electrically conductive fluids to form first and second mixtures respectively, said surfactant having an affinity for attaching to the microporous membrane;

filling the first compartment with the first mixture;

filling the second compartment with the second mixture;

forming an electrical circuit which includes an impedance, the microporous membrane, the first mixture and the second mixture;

applying a predetermined signal to the electrical circuit;

measuring a test voltage across the impedance;

selecting the predetermined amounts of surfactant in the first and second mixtures to prevent the mixtures from substantially wetting the pores of a non-defective microporous before measuring the test voltage across the impedance;

comparing the measured test voltage to a predetermined threshold value;

determining the microporous membrane to be defective if the measured test voltage exceeds the predetermined threshold value and determining the microporous membrane to be non-defective if the measured test voltage does not exceed the predetermined threshold value;

draining the first and second mixtures from the respective first and second compartments while maintaining surfactant deposited as a coating on the first and second surfaces of the microporous membrane; and air drying the microporous membrane for a predetermined drying time sufficient to eliminate residual first and second fluids from the microporous membrane after draining, wherein said surfactant reduces the surface tension between the microporous membrane and residual first and second fluids to establish the predetermined drying time for air drying the microporous membrane as less than the air drying time of the microporous membrane in the absence of surfactant.

15. A method as defined in claim 14, wherein the surfactant remains durably deposited to at least a portion of the first surface of the microporous membrane following the step of air drying the microporous membrane, said surfactant providing a bio-compatible coating for blood contacting the first surface of the microporous membrane.

16. A method as defined in claim 15 wherein the mass transfer device is a blood oxygenator.

17. A method as defined in claim 16 wherein:

the microporous membrane is a hollow fiber bundle;

the first surface of the microporous membrane is an exterior surface of the hollow fibers; and the second surface of the microporous membrane is an interior surface of the hollow fibers.

18. A method as defined in claim 16 wherein the microporous membrane is a flat sheet membrane.

19. A method as defined in claim 18 wherein the surfactant is polysorbate 80, NF (polyoxyethylene 20 sorbitan monooleate).

20. A method as defined in claim 19 wherein the predetermined drying time is less than 30 minutes.

21. A method as defined in claim 20 wherein the predetermined drying time is less than 15 minutes.

22. A method as defined in claim 19 wherein the first and second mixtures are pressurized to substantially the same pressure.

23. A method as defined in claim 19 wherein the first and second mixtures are substantially at ambient pressure.

24. A method as defined in claim 19 wherein:

the predetermined amount of the surfactant in the first mixture is within a range of approximately 0.010% to 0.100% by weight of the first electrically conductive fluid; and the predetermined amount of the surfactant in the second mixture is within a range of approximately 0.010% to 0.100% by weight of the second electrically conductive fluid.

25. A method as defined in claim 24 wherein:

the predetermined amount of the surfactant in the first mixture is approximately 0.025% by weight of the first electrically conductive fluid; and the predetermined amount of the surfactant in the second mixture is approximately 0.025% by weight of the second electrically conductive fluid.

26. A method of testing and coating a microporous membrane of a mass transfer device, the microporous membrane having opposing surfaces and pores extending between the surfaces, said method comprising the steps of:

contacting the opposing surfaces of the microporous membrane with electrically conductive fluids;

including a surfactant having fluid surface tension reducing characteristics in the electrically conductive fluid which contacts at least one surface of the microporous membrane;

conducting current through the electrically conductive fluids and the microporous membrane before the surfactant wets pores of the membrane;

correlating the current conducted to the physical integrity of the membrane;

draining the conductive fluid from the mass transfer device after the current is conducted; and drying the surfactant remaining on the membrane to form a surfactant coating on the membrane after the fluid is drained.

27. A method as defined in claim 26, wherein the surfactant remains durably deposited to at least a portion of a surface of the microporous membrane following the step of drying, said surfactant providing a bio-compatible coating for blood contacting a surface of the microporous membrane.

28. A method as defined in claim 26 wherein the surfactant is polysorbate 80, NF (polyoxyethylene 20 sorbitan monooleate).

29. A method as defined in claim 26 wherein drying is accomplished in less than 10 minutes.

30. A method as defined in claim 26 wherein the electrically conductive fluids contacting the opposing sides of the microporous membrane have substantially the same conductivity.

31. A method as defined in claim 26 wherein the electrically conductive fluids contacting the opposing sides of the microporous membrane are identical.

32. A method as defined in claim 26 wherein the electrically conductive fluids contacting the opposing sides of the microporous membrane are pressurized to substantially the same pressure when current is conducted through the membrane.

33. A method as defined in claim 26 wherein the first and second electrically conductive fluids are substantially at ambient pressure when current is conducted through the membrane.

34. A method as defined in claim 26 wherein the surfactant is included within a range of approximately 0.010% to 0.100% by weight in a conductive fluid.

35. A method as defined in claim 26 wherein the surfactant is included at approximately 0.025% by weight in a conductive fluid.

* * * * *